(12) United States Patent
Grata et al.

(10) Patent No.: US 8,157,747 B2
(45) Date of Patent: Apr. 17, 2012

(54) SINGLE-USE INDICATOR FOR A SURGICAL INSTRUMENT AND A SURGICAL INSTRUMENT INCORPORATING SAME

(75) Inventors: Paul John Grata, Hialeah, FL (US); Daniel Espinosa, Miami, FL (US); Alejandro Espinosa, Miami, FL (US)

(73) Assignee: Lary Research & Development, LLC, Miami, FL (US)

( * ) Notice: Subject to any disclaimer, the term of this patent is extended or adjusted under 35 U.S.C. 154(b) by 367 days.

(21) Appl. No.: 12/031,874

(22) Filed: Feb. 15, 2008

(65) Prior Publication Data

US 2009/0209907 A1    Aug. 20, 2009

(51) Int. Cl.
*A61B 5/00* (2006.01)

(52) U.S. Cl. ........ 600/574; 600/575; 600/583; 600/584; 604/318; 604/361; 604/403; 604/404

(58) Field of Classification Search .......... 600/583, 600/574, 584; 604/318, 361, 403, 404
See application file for complete search history.

(56) References Cited

U.S. PATENT DOCUMENTS

| | | | |
|---|---|---|---|
| 2,896,618 A * | 7/1959 | Schaefer | 602/47 |
| 2,936,760 A | 5/1960 | Gants | |
| 3,448,739 A | 6/1969 | Stark et al. | |
| 3,625,793 A | 12/1971 | Sheridan et al. | |
| 3,640,277 A * | 2/1972 | Adelberg | 604/141 |
| 3,791,933 A * | 2/1974 | Moyer et al. | 435/287.8 |
| 3,864,676 A * | 2/1975 | Macias et al. | 600/382 |
| 3,888,249 A | 6/1975 | Spencer | |
| 3,958,561 A * | 5/1976 | Bucalo | 600/575 |
| 3,995,623 A | 12/1976 | Blake et al. | |
| 4,022,216 A | 5/1977 | Stevens | |
| 4,055,180 A * | 10/1977 | Karami | 604/368 |
| 4,159,722 A * | 7/1979 | Walker | 137/496 |

(Continued)

FOREIGN PATENT DOCUMENTS

EP    0775500    5/1997

(Continued)

OTHER PUBLICATIONS

Banning G. Lary, "Varicose Veins and Intracutaneous Telangiectasi: Combined Treatment in 1,500 cases," The e Southern Medical Association, vol. 80, No. 9, pp. 1105-1110, Sep. 1987.

(Continued)

*Primary Examiner* — Nicholas Lucchesi
*Assistant Examiner* — Scott Medway
(74) *Attorney, Agent, or Firm* — Gordon & Jacobson, PC

(57) ABSTRACT

A single-use indicator is provided and is particularly well suited for use with a surgical catheter device. The indicator includes an absorbent filament or wick which is placed in a transparent or translucent indicator lumen of a multi-lumen catheter. The lumen is provided with at least one side port. When the catheter is inserted into a blood vessel, blood enters the indicator lumen through the side port and is absorbed by the filament, thus turning the filament red or purple in color. When the instrument is removed from the blood vessel, the stained filament is clearly visible as an indicator that the instrument has been used. Because the filament is trapped inside a lumen of a relatively long catheter, it is difficult or impossible to remove it during a remanufacturing process.

16 Claims, 2 Drawing Sheets

U.S. PATENT DOCUMENTS

| | | | |
|---|---|---|---|
| 4,198,981 A | 4/1980 | Sinnreich | |
| 4,274,423 A | 6/1981 | Mizuno et al. | |
| 4,318,410 A | 3/1982 | Chin | |
| 4,351,338 A * | 9/1982 | Langlois et al. | 604/515 |
| 4,436,098 A * | 3/1984 | Kaufman | 600/579 |
| 4,453,545 A | 6/1984 | Inoue | |
| 4,573,966 A | 3/1986 | Weikl et al. | |
| 4,583,967 A | 4/1986 | Harris | |
| 4,610,662 A | 9/1986 | Weikl et al. | |
| 4,636,195 A | 1/1987 | Wolinsky | |
| 4,655,746 A | 4/1987 | Daniels et al. | |
| 4,689,041 A | 8/1987 | Corday et al. | |
| 4,692,139 A | 9/1987 | Stiles | |
| 4,696,668 A | 9/1987 | Wilcox | |
| 4,705,502 A | 11/1987 | Patel | |
| 4,705,507 A | 11/1987 | Boyles | |
| 4,717,379 A | 1/1988 | Ekholmer | |
| 4,781,683 A * | 11/1988 | Wozniak et al. | 604/110 |
| 4,795,427 A | 1/1989 | Helzel | |
| 4,808,153 A | 2/1989 | Parisi | |
| 4,808,158 A * | 2/1989 | Kreuzer et al. | 604/500 |
| 4,832,688 A | 5/1989 | Sagae et al. | |
| 4,867,742 A | 9/1989 | Calderon | |
| 4,922,924 A | 5/1990 | Gambale et al. | |
| 4,927,418 A | 5/1990 | Dake et al. | |
| 4,968,306 A | 11/1990 | Huss et al. | |
| 4,983,166 A | 1/1991 | Yamawaki | |
| 4,995,863 A * | 2/1991 | Nichols et al. | 604/247 |
| 5,022,399 A | 6/1991 | Biegeleisen | |
| 5,030,210 A | 7/1991 | Alchas | |
| 5,033,998 A | 7/1991 | Corday et al. | |
| 5,046,503 A | 9/1991 | Schneiderman | |
| 5,047,013 A | 9/1991 | Rossdeutscher | |
| 5,085,635 A | 2/1992 | Cragg | |
| 5,087,244 A | 2/1992 | Wolinsky | |
| 5,090,960 A | 2/1992 | Don Michael | |
| 5,100,424 A | 3/1992 | Jang et al. | |
| 5,217,474 A | 6/1993 | Zacca et al. | |
| 5,219,335 A | 6/1993 | Willard et al. | |
| 5,246,423 A | 9/1993 | Farkas | |
| 5,250,034 A | 10/1993 | Appling et al. | |
| 5,279,546 A | 1/1994 | Mische et al. | |
| 5,286,254 A | 2/1994 | Shapland et al. | |
| 5,327,897 A * | 7/1994 | Andresen | 600/575 |
| 5,336,178 A | 8/1994 | Kaplan et al. | |
| 5,338,302 A | 8/1994 | Hasson | |
| 5,360,403 A | 11/1994 | Mische | |
| 5,395,352 A | 3/1995 | Penny | |
| 5,397,307 A | 3/1995 | Goodin | |
| 5,411,475 A | 5/1995 | Atala et al. | |
| 5,437,653 A * | 8/1995 | Gilman et al. | 604/378 |
| 5,533,516 A * | 7/1996 | Sahatjian | 600/562 |
| 5,536,250 A | 7/1996 | Klein et al. | |
| 5,554,114 A | 9/1996 | Wallace et al. | |
| 5,562,614 A | 10/1996 | O'Donnell | |
| 5,599,306 A | 2/1997 | Klein et al. | |
| 5,609,598 A | 3/1997 | Laufer et al. | |
| 5,611,775 A | 3/1997 | Machold et al. | |
| 5,628,730 A | 5/1997 | Shapland et al. | |
| 5,637,086 A | 6/1997 | Ferguson et al. | |
| 5,658,301 A | 8/1997 | Lemaitre et al. | |
| 5,674,282 A | 10/1997 | Cumming | |
| 5,676,962 A | 10/1997 | Cabrera | |
| 5,695,495 A | 12/1997 | Ellman et al. | |
| 5,709,653 A | 1/1998 | Leone | |
| 5,713,860 A | 2/1998 | Kaplan et al. | |
| 5,713,863 A | 2/1998 | Vigil et al. | |
| 5,730,136 A | 3/1998 | Laufer et al. | |
| 5,779,673 A * | 7/1998 | Roth et al. | 604/101.03 |
| 5,800,407 A | 9/1998 | Eldor | |
| 5,800,408 A | 9/1998 | Strauss et al. | |
| 5,810,847 A | 9/1998 | Laufer et al. | |
| 5,833,650 A | 11/1998 | Imran | |
| 5,840,066 A | 11/1998 | Matsuda et al. | |
| 5,861,005 A * | 1/1999 | Kontos | 606/219 |
| 5,882,332 A | 3/1999 | Wijay | |
| 5,902,266 A | 5/1999 | Leone et al. | |
| 5,921,954 A | 7/1999 | Mohr, Jr. et al. | |
| 5,947,977 A | 9/1999 | Slepian et al. | |
| 5,971,942 A * | 10/1999 | Gu et al. | 600/582 |
| 5,993,382 A | 11/1999 | Pruitt, Sr. | |
| 6,014,589 A | 1/2000 | Farley et al. | |
| 6,033,397 A | 3/2000 | Laufer et al. | |
| 6,033,398 A | 3/2000 | Farley et al. | |
| 6,036,687 A | 3/2000 | Laufer et al. | |
| 6,048,332 A | 4/2000 | Duffy et al. | |
| 6,063,069 A | 5/2000 | Cragg et al. | |
| 6,071,251 A * | 6/2000 | Cunningham et al. | 600/584 |
| 6,071,277 A | 6/2000 | Farley et al. | |
| 6,074,356 A | 6/2000 | Starkey et al. | |
| 6,096,021 A | 8/2000 | Helm et al. | |
| 6,096,054 A | 8/2000 | Wyzgala et al. | |
| 6,102,904 A | 8/2000 | Vigil et al. | |
| 6,103,769 A | 8/2000 | Kelm | |
| 6,113,576 A | 9/2000 | Dance et al. | |
| 6,117,105 A | 9/2000 | Bresnaham et al. | |
| 6,126,641 A * | 10/2000 | Shields | 604/192 |
| 6,135,991 A | 10/2000 | Muni et al. | |
| 6,152,899 A | 11/2000 | Farley et al. | |
| 6,165,172 A | 12/2000 | Farley et al. | |
| 6,179,832 B1 | 1/2001 | Jones et al. | |
| 6,190,357 B1 | 2/2001 | Ferrari et al. | |
| 6,200,312 B1 | 3/2001 | Zikorus et al. | |
| 6,219,574 B1 * | 4/2001 | Cormier et al. | 604/20 |
| 6,241,689 B1 * | 6/2001 | Chard et al. | 600/584 |
| 6,264,633 B1 | 7/2001 | Knorig | |
| 6,290,689 B1 | 9/2001 | Delaney et al. | |
| 6,371,942 B1 | 4/2002 | Schwartz et al. | |
| 6,398,780 B1 | 6/2002 | Farley et al. | |
| 6,409,716 B1 | 6/2002 | Sahatjian et al. | |
| 6,440,097 B1 | 8/2002 | Kupiecki | |
| 6,458,076 B1 | 10/2002 | Pruitt | |
| 6,482,172 B1 | 11/2002 | Thramann | |
| 6,485,500 B1 | 11/2002 | Kokish et al. | |
| 6,488,672 B1 | 12/2002 | Dance et al. | |
| 6,503,185 B1 | 1/2003 | Waksman et al. | |
| 6,520,975 B2 | 2/2003 | Branco | |
| 6,527,759 B1 | 3/2003 | Tachibana et al. | |
| 6,527,761 B1 | 3/2003 | Soltesz et al. | |
| 6,528,325 B1 * | 3/2003 | Hubscher et al. | 436/518 |
| 6,533,767 B2 | 3/2003 | Johansson et al. | |
| 6,538,026 B1 | 3/2003 | Krall et al. | |
| 6,544,221 B1 | 4/2003 | Kokish et al. | |
| 6,558,367 B1 | 5/2003 | Cragg et al. | |
| 6,569,146 B1 | 5/2003 | Werner et al. | |
| 6,602,241 B2 | 8/2003 | Makower et al. | |
| 6,638,243 B2 | 10/2003 | Kupiecki | |
| 6,689,126 B1 | 2/2004 | Farley et al. | |
| 6,695,827 B2 * | 2/2004 | Chen et al. | 604/385.01 |
| 6,699,272 B2 | 3/2004 | Slepian et al. | |
| 6,726,674 B2 | 4/2004 | Leu | |
| 6,730,299 B1 | 5/2004 | Tayot et al. | |
| 6,764,461 B2 | 7/2004 | Mickley et al. | |
| 6,824,975 B2 * | 11/2004 | Hubscher et al. | 435/4 |
| 6,958,054 B2 * | 10/2005 | Fitzgerald | 604/162 |
| 6,984,225 B2 * | 1/2006 | Raidel et al. | 604/385.101 |
| 7,041,057 B1 * | 5/2006 | Faupel et al. | 600/365 |
| 7,077,836 B2 | 7/2006 | Lary et al. | |
| 7,176,344 B2 * | 2/2007 | Gustafson et al. | 604/361 |
| 7,329,237 B2 | 2/2008 | Yokoyama et al. | |
| 7,335,023 B2 * | 2/2008 | Mahlmann | 433/96 |
| 2002/0055730 A1 | 5/2002 | Yachia et al. | |
| 2002/0077589 A1 | 6/2002 | Tessari | |
| 2002/0133140 A1 | 9/2002 | Moulis | |
| 2002/0177870 A1 | 11/2002 | Sepetka et al. | |
| 2003/0004452 A1 | 1/2003 | Lenker | |
| 2003/0045860 A1 | 3/2003 | Leu | |
| 2003/0051735 A1 * | 3/2003 | Pavcnik et al. | 128/831 |
| 2003/0082243 A1 | 5/2003 | Harman et al. | |
| 2003/0083615 A1 | 5/2003 | Dance et al. | |
| 2003/0120201 A1 | 6/2003 | Abergel | |
| 2003/0120256 A1 | 6/2003 | Banning | |
| 2004/0015159 A1 | 1/2004 | Slater | |
| 2004/0049169 A1 | 3/2004 | Fischell | |
| 2004/0220547 A1 | 11/2004 | Heruth et al. | |
| 2005/0107738 A1 | 5/2005 | Slater | |
| 2005/0113798 A1 | 5/2005 | Slater | |

| | | | |
|---|---|---|---|
| 2006/0015071 A1* | 1/2006 | Fitzgerald | 604/168.01 |
| 2006/0095015 A1 | 5/2006 | Hobbs et al. | |
| 2006/0149218 A1 | 7/2006 | Slater | |
| 2007/0135791 A1 | 6/2007 | Slater | |
| 2007/0196414 A1* | 8/2007 | Hammarsten et al. | 424/422 |
| 2008/0107564 A1* | 5/2008 | Sternberg et al. | 422/55 |

FOREIGN PATENT DOCUMENTS

| | | |
|---|---|---|
| WO | WO 2004/033013 | 4/2004 |
| WO | WO 2004/058336 | 7/2004 |
| WO | WO 2004/058337 | 7/2004 |
| WO | WO2004/071612 | 8/2004 |
| WO | WO2006/023203 | 3/2006 |
| WO | WO2006/076699 | 7/2006 |

OTHER PUBLICATIONS

"Y Connectors," DeRoyal, Powell, TN Revised May 2002.

BTG Press Release, "BTG Plc Analyst & Investor Briefing" http://www.btgplc.com/news_content/mn_corporate_release.cfm?doc_id=49&CFID=4795&CFTOKEN=75848369, Sep. 8, 2000.

BTG Press Release, "Interim Results for the Six Months Ended Sep. 30, 2000," available at http://www.btgplc.com/news_content/mn_corporate_release.cfm?doc_id=50&CFID=47958,CFTOKEN=75848369, Nov. 23, 2000.

BTG Press Release, "MCA approves pivotal Phase III trials for Varisolve® in the UK," available at http://www.btgplc.com/news_content/mn_pharmaceutical_release.dfm?doc_id=417&CFID=4795&CFTOKEN=75848369, Feb. 27, 2001.

BTG Press Release, "BTG Reports Positive Results from UK Varisolve® Trials" available at http://www.btgplc.com/news_content/mn_pharmaceutical_release.dfm?doc_id=518&CFID=4798&, CFTOKEN=75848369, May 15, 2001.

BTG Press Release, "Preliminary Results for the Year Ended Mar. 31, 2001," available at http://www.btgplc.com/news/12062001Prelims.html, Jun. 12, 2001.

Min, Robert J., et al., "Transcatheter Duplex Ultrasound-Guided Sclerotherapy for Treatment of Greater Saphenous Vein Reflux: Premilinary Report," Dermatol Surg, 26: 410-414, May 2000.

Downloaded from Internet, information on RITA—radiofrequency Interstitial Tissue Ablation (medical devices for minimally invasive surgery), available at www.ritamedical.com/products.html,1pg.

"Protecting Against Unfair Competitionin the US from Surgical Instruments Reprocessors" Report by William E. Gallagher, © 2006 Frost Brown Todd LLC.

* cited by examiner

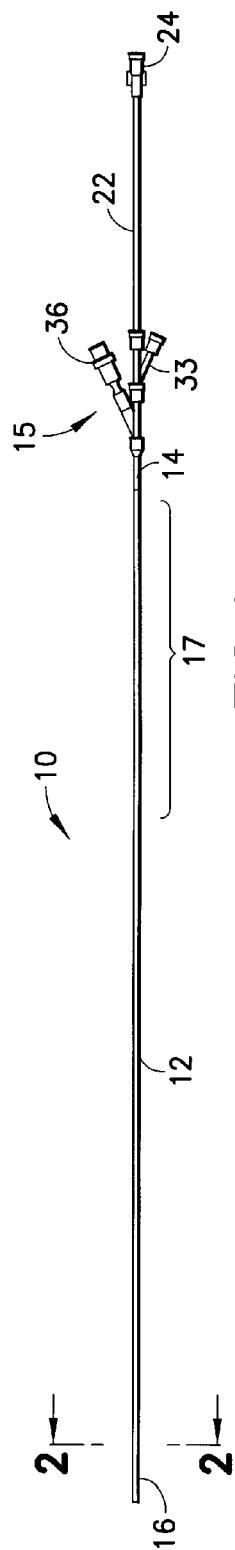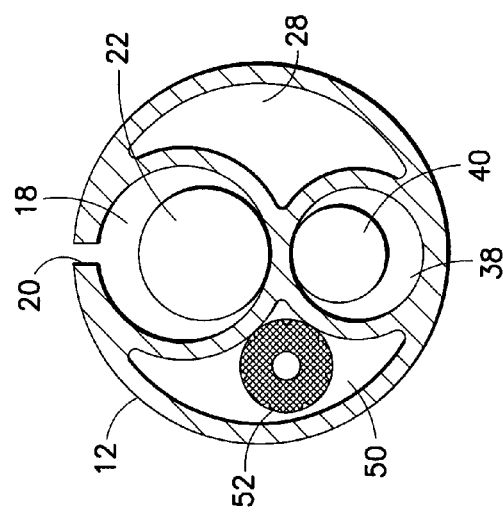

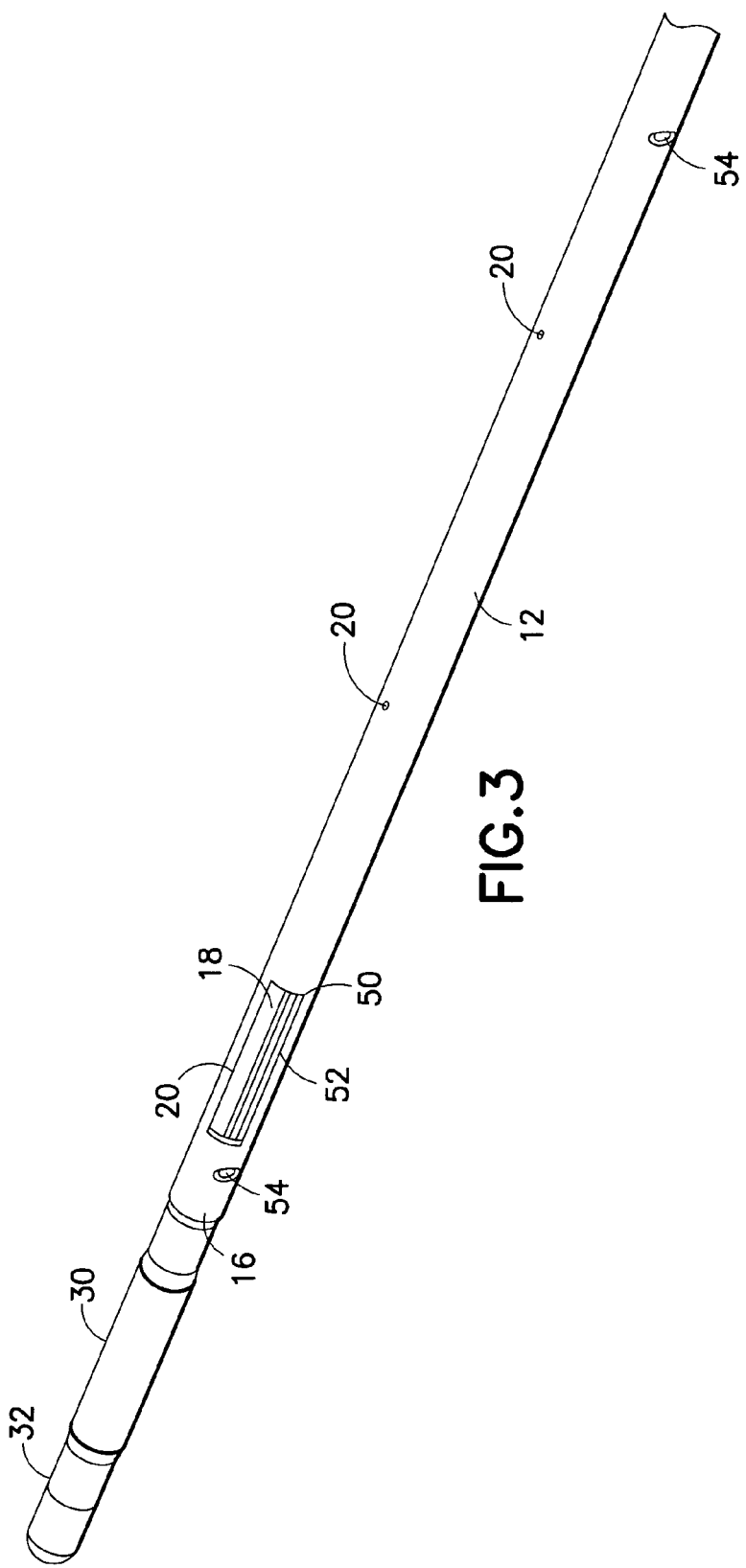

SINGLE-USE INDICATOR FOR A SURGICAL INSTRUMENT AND A SURGICAL INSTRUMENT INCORPORATING SAME

INCORPORATION BY REFERENCE

The following co-owned patents and applications, the complete disclosures of which are incorporated by reference herein, are useful in understanding the applications of the present invention: Ser. Nos. 10/358,523 [SYN-053CIP]; 10/621,943 [SYN-079]; 10/544,082 [SYN-080]; 10/922,221 [VRX-001CIP1]; 10/922,123 [VRX-001CIP2]; 11/624,412 [VRX-006]; 11/624,431 [VRX-007]; and 11/675,919 [VRX-011], U.S. Pat. No. 7,077,836 entitled "Methods and Apparatus for Sclerosing the Wall of a Varicose Vein", published International Application WO 2006/076699, entitled "Valve System for a Medical Device Having an Inflatable Member", published International Application WO 2006/023203, entitled "An Occludable Intravascular Catheter for Drug Delivery and Method of Using the Same", and published International Application WO 2004/071612, entitled "Methods and Apparatus for Treating the Interior of a Blood Vessel".

BACKGROUND OF THE INVENTION

1. Field of the Invention

This invention relates broadly to surgical instruments. More particularly, this invention relates to single-use surgical instruments. Most particularly this invention relates to an indicator which indicates whether a surgical instrument has been used.

2. State of the Art

The manufacture of surgical instruments comprises a very large industry. Some surgical instruments are designed for multiple use. That is, they are cleaned and sterilized after use for use again. Single-use surgical instruments have been available for more than twenty years. These surgical instruments are used only once and then discarded as medical waste.

There is a great desire to reduce the per procedure cost of surgery. This has given rise to a substantial secondary market for companies engaged in salvaging, cleaning, and sterilizing used single-use surgical instruments.

SUMMARY OF THE INVENTION

The invention provides a single-use indicator for a single-use surgical instrument.

The invention provides an indicator that clearly indicates that a surgical instrument has been used.

The invention provides a relatively tamper proof single-use indicator for a surgical instrument.

The invention provides a single-use indicator which is easy to incorporate into a single-use surgical instrument.

The invention provides a single-use indicator which is inexpensive.

The invention provides a single-use indicator which is reliable.

The invention also provides a single-use surgical instrument which incorporates a single-use indicator.

The invention provides a single-use indicator which is particularly well suited for use with a surgical catheter device such as the devices disclosed in the previously incorporated co-owned applications and patent. The indicator includes an absorbent filament or wick which is placed in a transparent or translucent indicator lumen of a multi-lumen catheter. The lumen is provided with at least one side port. When the catheter is inserted into a blood vessel, blood enters the indicator lumen through the side port and is absorbed by the filament, thus turning the filament red or purple in color. When the instrument is removed from the blood vessel, the stained filament is clearly visible as an indicator that the instrument has been used. Because the filament is trapped inside a lumen of a relatively long catheter, it is difficult or impossible to remove it during a remanufacturing process.

An exemplary single-use surgical instrument according to the invention includes an elongate body having a proximal end, a distal end, and a plurality of lumens extending therethrough. The lumens include an infusion lumen, an occlusion balloon inflation lumen, a guide wire lumen and an indicator lumen according to the invention. Along a length of the elongate body are a plurality of infusion holes in valved communication with the infusion lumen, and a valve member is movable inside the infusion lumen from a first position in which some of the infusion holes are blocked to a second position where fewer of the infusion holes are blocked. An inflatable occlusion balloon is provided at the distal end of the elongate body and is in fluid communication with the inflation lumen. The guide wire lumen has openings at both its proximal and distal ends. The indicator lumen is filled, at least partially, with an absorbent filament or wick and at least one, preferably a plurality of side ports providing fluid communication between the environment and the indicator lumen. The presently preferred material for the filament is 100% fine silk. The elongate body is preferably a single extruded piece of polymeric material (preferably nylon) and is either transparent or translucent to the extent that the filament inside the indicator lumen can be clearly seen. The ends of the indicator lumen are closed by sonic welding or other means so that the filament cannot be removed. The side ports and the filament have relative dimensions such that the filament cannot be removed from the indicator lumen by pulling it through a side port. Preferably. The ends of the silk thread are anchored with glue before the ends of the indicator lumen are closed.

Additional advantages of the invention will become apparent to those skilled in the art upon reference to the detailed description taken in conjunction with the provided figures.

BRIEF DESCRIPTION OF THE DRAWINGS

FIG. 1 is a plan view of a single-use surgical instrument according to the invention;

FIG. 2 is an enlarged sectional view taken along line 2-2 in FIG. 1; and FIG. 3 is an enlarged broken and partially cut away view of the distal end of the instrument of FIG. 1.

DETAILED DESCRIPTION OF THE PREFERRED EMBODIMENT

Turning now to FIGS. 1-3, an exemplary single-use surgical instrument 10 incorporating the invention is of the type described in the previously incorporated applications and patent. The instrument 10, which is for treating the interior of a blood vessel, includes an elongate body 12 having a proximal end 14, a distal end 16. and an infusion lumen 18 extending there-through (FIGS. 2 and 3). A plurality of infusion holes 20 (FIG. 3) are in valved communication with the infusion lumen 18. An elongate valve member 22 (FIG. 2) having a distal sealing element (not shown) is movable inside said infusion lumen 18. The elongate valve member is a non-perforate cylinder having a lumen (not shown). By moving the valve member proximally or distally more or fewer elution holes are unblocked.

As seen best in FIG. 1, the proximal end of the elongate valve member 22 is provided with an infusion port 24 (a luer lock). The proximal end 14 of the elongate body 12 is provided with a hub 15. As seen best in FIG. 2, the elongate body 12 is provided with a second lumen 28. The distal end of the second lumen 28 terminates inside an inflatable balloon 30 (FIG. 3). An atraumatic tip 32 is coupled to the distal end of the balloon 30. The proximal end of the second lumen 28 is coupled to the side port 36 of the hub 15 shown in FIG. 1. The side port 36 includes a luer with a luer activated valve for connecting a balloon inflation syringe (not shown). The elongate body 12 is also provided with a guide wire lumen 38 (FIG. 2) for a guide wire 40. The guide wire lumen 38 extends from a hole in the tip 32 to the side port 33 of the hub 15. The side port 33 is provided with a plug cap to close off the guide wire lumen when not in use.

According to the invention, the elongate body 12 is provided with a fourth lumen 50 for an absorbent filament 52. The presently preferred filament is an eighteen inch long bundle of six strands of 100% silk each having a diameter of 0.006 inch. The lumen 50 is provided with at least one, and preferably a plurality of side ports 54 (FIG. 3). The lumen 50 and the filament 52 preferably extend the entire length of the elongate body 12. However, the invention will still function correctly provided that the lumen 50, the filament 52, and at least one of the side ports 54 are located somewhere along the length of the elongate body which is known to enter a blood vessel during surgery. For example, the distal end 16 of the elongate body 12 is certain to be introduced into a blood vessel. However, depending on the patient, a proximal length, e.g. 17 in FIG. 1, may never enter a blood vessel. Therefore, it is preferred that, if the filament 52 does not extend the entire length of the elongate body, it should extend proximally from the distal end 16 of the elongate body 12 for a visible length. The lumen 50 containing the filament is preferably sealed at its ends by sonic welding or other means so that the filament cannot be removed. According to the presently preferred embodiment, the ends of the filament are anchored with glue before the lumen is sealed. The side ports 54 and the filament 52 have relative dimensions such that the filament cannot be removed from the indicator lumen by pulling it through a side port.

The method of utilizing the apparatus 10 generally includes introducing the elongate body 12 over guide wire 40 into a blood vessel and locating the distal end 16 at a predetermined location in the blood vessel and the guide wire 40 is removed. The balloon 30 is then inflated to occlude the blood vessel. At some point before the next step, the elongate valve member 22 is adjusted (i.e. the distal sealing element is located to select a treatment length). Then, a treating agent is injected into the infusion port 24, through the elongate valve member 22 and into the lumen 18 whereupon the agent exits the elution holes 20 distal of the sealing element. While the elongate body 12 is present in the blood vessel, blood enters the side ports 54 of the lumen 50 and is absorbed by the filament 52. When the desired quantity of treating agent has been infused into the blood vessel, the balloon 30 is deflated and the elongate body 12 is removed. Once removed from the blood vessel, the instrument 10 will contain clearly visible evidence that it has been used, i.e. a red or purplish stripe extending the length of the filament 52, preferably the entire length of the elongate body 12.

There have been described and illustrated herein a single use indicator for a surgical instrument and a single-use surgical instrument incorporating same. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed.

What is claimed is:

1. A surgical instrument, comprising:
an elongate body having a longitudinal axis, a distal end, an exterior wall defining a transparent or translucent indicator lumen, and at least one side port disposed entirely proximal of said distal end in said exterior wall, said side port laterally offset from said longitudinal axis and extending through said exterior wall in a transverse direction relative to said longitudinal axis, said side port in fluid communication with said indicator lumen;
an occlusion balloon coupled to said body, wherein said body defines a second lumen that is in fluid communication with said occlusion balloon; and
an absorbent material disposed in said indicator lumen, such that when said body is immersed in blood, blood flows into said at least one side port to said indicator lumen and is absorbed by said absorbent material.

2. A surgical instrument according to claim 1, wherein:
said absorbent material is a filament.

3. A surgical instrument according to claim 2, wherein:
said filament is silk.

4. A surgical instrument according to claim 1, wherein:
said absorbent material extends substantially the entire length of said indicator lumen.

5. A surgical instrument according to claim 4, wherein:
said indicator lumen extends substantially the entire length of said body.

6. A surgical instrument according to claim 1, wherein:
said body defines a third lumen having a plurality of infusion ports.

7. A surgical instrument according to claim 1, wherein said occlusion balloon is disposed at said distal end of said elongate body.

8. A surgical instrument according to claim 1, wherein:
said body defines a guide wire lumen adapted to receive a guide wire.

9. An apparatus for treating blood vessels, comprising:
an elongate body having a proximal end, a distal end, a longitudinal axis, and an infusion lumen extending there-through, the body having an exterior wall defining a transparent or translucent indicator lumen and at least one side port, said side port laterally offset from said longitudinal axis and extending through said exterior wall in a transverse direction relative to said longitudinal axis, said side port disposed proximal of said distal end in said exterior wall and in fluid communication with said indicator lumen;
a plurality of spaced apart infusion holes along a length of the infusion lumen;
an elongate valve member which is movable inside said infusion lumen from a first position in which access to some but not all of the infusion holes are blocked by said elongate valve member to a second position where access to fewer of the infusion holes are blocked by said elongate valve member;
an infusion port coupled to said elongate valve member, such that infusion fluid injected into said infusion port flows through said elongate valve member, into a portion of said infusion lumen; and an absorbent material disposed in said indicator lumen, such that, when said body is immersed in blood, blood flows into said at least one side port to said indicator lumen and is absorbed by said absorbent material and said absorbent material can be seen inside said indicator lumen.

10. An apparatus according to claim 9, wherein:
said absorbent material is a filament.

11. An apparatus according to claim 10, wherein:
said filament is silk.

12. An apparatus according to claim 9, wherein:
said absorbent material extends substantially the entire length of said indicator lumen.

13. An apparatus according to claim 12, wherein:
said lumen extends substantially the entire length of said body.

14. An apparatus according to claim 9, further comprising:
an occlusion balloon coupled to said body, wherein said body defines an inflation lumen in fluid communication with said occlusion balloon.

15. An apparatus according to claim 9, wherein:
said body defines a guide wire lumen adapted to receive a guide wire.

16. An apparatus according to claim 14, wherein:
said occlusion balloon is disposed at said distal end of said elongate body.

\* \* \* \* \*